United States Patent
Morrison et al.

(10) Patent No.: US 10,487,042 B2
(45) Date of Patent: Nov. 26, 2019

(54) METHOD FOR SOLVENT-FREE DECARBOXYLATION OF AMINO ACIDS VIA IMINE FORMATION

(71) Applicant: University of Georgia Research Foundation, Inc., Athens, GA (US)

(72) Inventors: Richard W. Morrison, Watkinsville, GA (US); Douglas Michael Jackson, Athens, GA (US); Daniel Richard Morrison, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/027,487

(22) Filed: Jul. 5, 2018

(65) Prior Publication Data

US 2018/0312461 A1    Nov. 1, 2018

Related U.S. Application Data

(63) Continuation-in-part of application No. 15/249,719, filed on Aug. 29, 2016, now Pat. No. 10,118,898, which is a continuation-in-part of application No. 14/210,655, filed on Mar. 14, 2014, now Pat. No. 9,452,954.

(60) Provisional application No. 61/783,052, filed on Mar. 14, 2013.

(51) Int. Cl.
*C07C 209/78* (2006.01)
*C07C 209/68* (2006.01)

(52) U.S. Cl.
CPC .......... *C07C 209/78* (2013.01); *C07C 209/68* (2013.01)

(58) Field of Classification Search
None
See application file for complete search history.

(56) References Cited

U.S. PATENT DOCUMENTS

| | | |
|---|---|---|
| 6,403,806 B1 | 6/2002 | Yeh et al. |
| 7,485,756 B2 | 2/2009 | Omeis et al. |
| 2008/0214864 A1 | 9/2008 | Omeis et al. |
| 2013/0202703 A1 | 8/2013 | Sadano |

FOREIGN PATENT DOCUMENTS

| | | |
|---|---|---|
| EP | 1586553 | 10/2005 |
| EP | 1586553 B1 | 4/2009 |
| JP | 2001220372 | 8/2001 |
| WO | 2013008256 | 1/2013 |

OTHER PUBLICATIONS

Galat, A.; Friedman, H.L . . . A New Method for the Isolation of Histamine. J. Am. Chem. Soc. 1949. 71, 3976.

Hashimoto, M.; Eda, Y.; Osani, Y.; Iwai, T.; Aoki, S . . . A Novel Decarboxylation of α-Amino Acids. A Facile Method of Decarboxylation by the Use of 2-Cyclohexen-1-One as a Catalyst. Chem. Lett. 1986, 6, 893.

Martins, C.P.B., et al. Fingerprint analysis of thermolytic decarboxylation of tryptophan to tryptamine catalyzed by natural oilsJ. Chromatogr. A. 2008, 1210, 115.

Bhatia, Sumeet Kaur; Samdhian, Varsha; Kaur, Balbir. Bis-dihydropyrimidines: Catalyst-free, Microwave-assisted Organic Synthesis, Characterization and In Vitro Biological Screenings. Journal of Heterocyclic Chemistry (2018), 55 (4), 935-942.

Belouezzane, Chiraz; Pinto, Angelo C.; Lima, Antonio L. S.; Miranda, Fabio S. Microwave assisted organic synthesis of benzophenothiazines: Photophysical and DFT calculations studies. Journal of Luminescence (2017), 192, 1139-1148.

Rodriguez, Antonio M.; Prieto, Pilar; de la Hoz, Antonio; Diaz-Ortiz, Angel; Martin, D. Raul; Garcia, Jose I. Influence of Polarity and Activation Energy in Microwave-Assisted Organic Synthesis (MAOS). ChemistryOpen (2015), 4(3), 308-317.

Aravind, K.; Arram, Ganesh; Ashok, D. Efficient solvent-free microwave assisted organic synthesis of 1-(2,4-dihydroxy-5-[3-imidazol-1-yl-3-aryl-propionyl]}-3-aryl-propenone and their antibacterial activity. Journal of Chemical and Pharmaceutical Research (2013), 5(6), 34-39.

Ceron-Camacho, Ricardo; Aburto, Jorge A.; Montiel, Luisa E.; Martinez-Palou, Rafael. Microwave-assisted organic synthesis versus conventional heating. A comparative study for Fisher glycosidation of monosaccharides. Comptes Rendus Chimie (2013), 16(5), 427-432.

de Souza, Rodrigo Octavio M. A.; Souter de M. e Miranda, Leandro. Microwave assisted organic synthesis: a history of success in Brazil. Quimica Nova (2011), 34(3), 497-506.

Kremsner, Jennifer M.; Kappe, C. Oliver. Microwave-assisted organic synthesis in near-critical water at 300° C.—a proof-of-concept study. European Journal of Organic Chemistry (2005), (17), 3672-3679.

Wang, Yunpu; Liu, Yuhuan; Ruan, Rongsheng; Wen, Pingwei; Wan, Yiqin; Zhang, Jinsheng. Microwave-assisted decarboxylation of sodium oleate and renewable hydrocarbon fuel production. China Petroleum Processing and Petrochemical Technology (2013), 15(3), 19-27.

Frederiksen, Lottie B.; Grobosch, Thomas H.; Jones, John R.; Lu, Shui-Yu; Zhao, Chao-Cheng. Microwave enhanced decarboxylation of aromatic carboxylic acids: improved deuteration/tritiation potential. Journal of Chemical Research, Synopses (2000), (1), 42-43.

Jones, Graham B.; Chapman, Brant J. Decarboxylation of indole-2-carboxylic acids: improved procedures. Journal of Organic Chemistry (1993), 58(20), 5558-9.

(Continued)

*Primary Examiner* — Kamal A Saeed

(74) *Attorney, Agent, or Firm* — Thomas|Horstemeyer, LLP; Christopher Linder; Heather Gorman

(57) ABSTRACT

The present application provides solvent-free methods for decarboxylation of amino acids via imine formation with a ketone, enone, enal, aldehyde co-reagent or combination thereof, under heated conditions, with optional recovery of the co-reagent and/or co-reagent byproduct.

21 Claims, 3 Drawing Sheets

(56) References Cited

OTHER PUBLICATIONS

Jackson, Douglas M.; Ashley, Robert L.; Brownfield, Callan B.; Morrison, Daniel R.; Morrison, Richard W. Rapid Conventional and Microwave-Assisted Decarboxylation of L-Histidine and Other Amino Acids via Organocatalysis with R-Carvone Under Superheated Conditions. Synthetic Communications (2015), 45(23), 2691-2700.
Fanny Araceli Cabrera-Rivera, Luis Gabriel Hernández-Vázquez, Patricia Flores-Sánchez, Maria Durán-Galván, Jaime Escalante. Solvent- and Catalyst-Free Microwave-Assisted Decarboxylation of Malonic Acid Derivatives. Green and Sustainable Chemistry vol. 07 No. 04(2017), Article ID:80316, 11 pages.
M. Hashimoto, Y. Eda, Y. Osanai, T. Iwai, and S. Aoki. Amino Acid Decarboxylation Catalyzed by 2-Cyclohexen-1-One. Chemistry Letters 893-896 (1986).
Ronaldo N. de Oliveira, Joa~o R. de Freitas Filho and Rajendra M. Srivastava. Microwave-induced synthesis of 2,3-unsaturated O-glycosides under solvent-free conditions. Tetrahedron Letters 43 (2002) 2141-2143.
Laval, Gilles & Golding, Bernard T. One-pot Sequence for the Decarboxylation of a-Amino Acids, Synlett 2003, No. 4, Print: Dec. 3, 2003.
Cynthia Lynn Zara, Thomas Jin & Raymond J. Giguere (2000) Microwave Heating in Organic Synthesis: Decarboxylation of Malonic Acid Derivatives in Water, Synthetic Communications, 30:12, 2099-2104.
Jiadi Zhou, Huan Liu, Zhaoyong Li, Can Jin, Weike Su. Aldehyde-induced metal-free decarboxylation of a-amino acids to synthesize N-alkyl-b-alkenyl cyclic amines with high stereoselectivity, Tetrahedron Letters 58 (2017) 3174-3177.
Al-Sayyab, A. F.; Lawson, Alexander. Schiff bases. I. Thermal decarboxylation of α-amino acids in the presence of ketones. Journal of the Chemical Society [Section] C: Organic (1968), (4), 406-10.
Al-Sayyab, A. F.; Lawson, Alexander; Stevens, J. O. Schiff bases. II. Ketimines prepared by decarboxylation of α-amino acids in the presence of ketones and their reaction and that of aldimines with phenyl isocyanate. Journal of the Chemical Society [Section] C: Organic (1968), (4), 411-15.
Kalyankar, G. D.; Snell, Esmond E. Pyridoxal-catalyzed decarboxylation of amino acids. Biochemistry (1962), 1(4), 594-600.
Aydogan, Feray; Demir, Ayhan S. Clean and efficient microwave-solvent-free conversion of homochiral amines, α-amino alcohols and α-amino acids to their chiral 2-substituted pyrrole derivatives. Tetrahedron (2005), 61(12), 3019-3023.
Yorur-Goreci, Cigdem; Demir, Zulal; Altas, Nilay. Green synthesis of new amino acid schiff bases and their biological activities. Journal of the Turkish Chemical Society, Section A: Chemistry (2016), 3(3), 15-26.
Chen, Ying-Ying; Chang, Li-Te; Chen, Hung-Wei; Yang, Chia-Ying; Hsin, Ling-Wei. Fast and Facile Synthesis of 4-Nitrophenyl 2-Azidoethylcarbamate Derivatives from N-Fmoc-Protected α-Amino Acids as Activated Building Blocks for Urea Moiety-Containing Compound Library. ACS Combinatorial Science (2017), 19(3), 131-136.
Xiang, Zhang. Aromatic aldehyde-catalyzed gas-phase decarboxylation of amino acid anion via imine intermediate: An experimental and theoretical study. Journal of Molecular Structure 1049 (2013) 149-156.
Zamora, Rosario; Leon, M. Mercedes; Hidalgo, Francisco J. Oxidative versus Non-oxidative Decarboxylation of Amino Acids: Conditions for the Preferential Formation of Either Strecker Aldehydes or Amines in Amino Acid/Lipid-Derived Reactive Carbonyl Model Systems. Journal of Agricultural and Food Chemistry (2015), 63(36), 8037-8043.
Douglas D. Young, Jessica Torres-Kolbus, Alexander Deiters. Bioorganic & Medicinal Chemistry Letters 18 (2008) 5478-5480.
Marianne Stenberg, Gyorgy Marko-Varga, Rickard Oste. Racemization of amino acids during classical and microwave oven hydrolysis—application to aspartame and a Maillard reaction system. Food Chemistry 74 (2001) 217-224.
Avan, Ilker. Microwave-assisted synthesis of 2,2'-azopyridine-labeled amines, amino acids, and peptides. Synthesis (2016), 48(3), 365-378.
Rheem A. Totah and Robert P. Hanzlik. Non-Oxidative Decarboxylation of Glycine Derivatives by a Peroxidase. J. Am. Chem. Soc. 2002, 124, 10000-10001.
Lemuel Pérez-Picaso 1, Jaime Escalante 1, Horacio F. Olivo 2 and Maria Yolanda Rios. Efficient Microwave Assisted Syntheses of 2,5-Diketopiperazines in Aqueous Media. Molecules 2009, 14, 2836-2849; doi:10.3390/molecules14082836.
Masao Fujimaki, Nguyen Van Chuyen & Tadao Kurata (1971) Studies on the Decarboxylation of Amino Acids with Glyoxal, Agricultural and Biological Chemistry, 35:13, 2043-2049, DOI: 10.1080/00021369.1971.10860189.

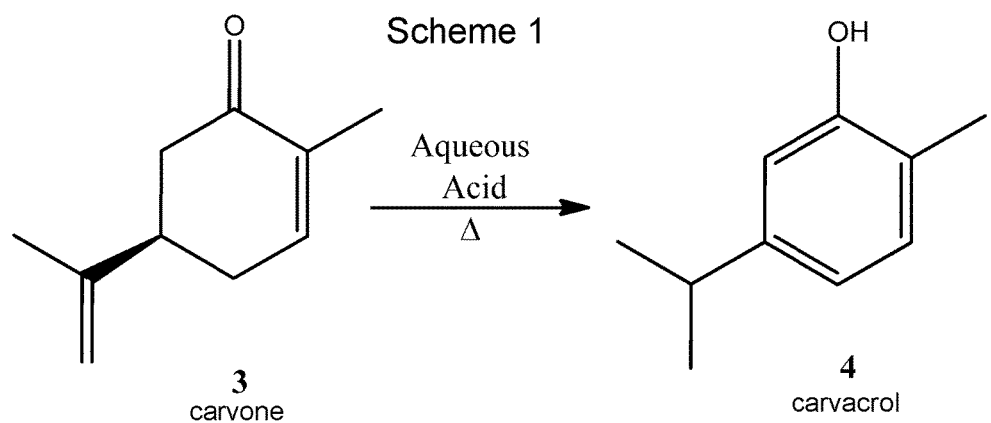
FIG. 1
FIG. 2
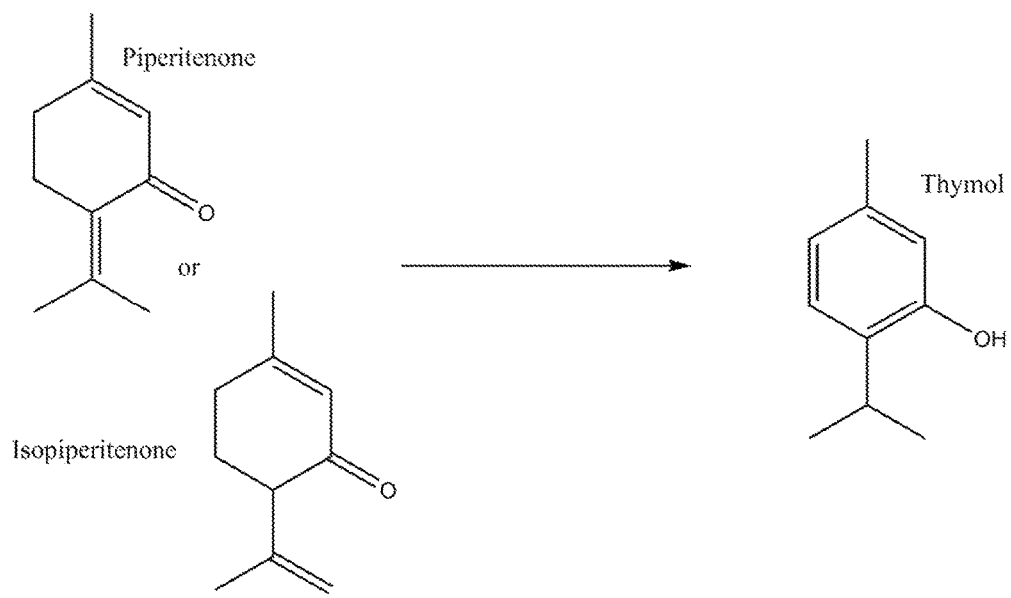

Xylenols

Ethylmethylphenols

Other examples:

METHOD FOR SOLVENT-FREE DECARBOXYLATION OF AMINO ACIDS VIA IMINE FORMATION

CROSS-REFERENCE TO RELATED APPLICATION

This application is a Continuation-in-part of U.S. patent application entitled "Method for Decarboxylation of Amino Acids Via Imine Formation", Ser. No. 15/249,719 filed Aug. 29, 2016, which was a Continuation-in-part of U.S. patent application entitled "Method for Decarboxylation of Amino Acids Via Imine Formation", Ser. No. 14/210,655 filed Mar. 14, 2014, issued as U.S. Pat. No. 9,452,954, which claims priority to and the benefit of U.S. provisional patent application entitled "Method for Decarboxylation of Amino Acids Via Imine Formation", Ser. No. 61/783,052 filed Mar. 14, 2013, all of which are incorporated herein by reference in their entirety.

BACKGROUND

Decarboxylation of amino acids is an important synthetic route to biologically active amines and other useful byproducts. Current procedures for synthesis of biologically relevant amines often suffer from extremely long reaction times, can require high boiling point solvents and extremely high reaction temperatures, and difficulty with solvent and byproduct removal.

Decarboxylation of amino acids is a long-known reaction for the production of biologically active amines and their derivatives, which find multiple applications. Some conventional methods involves high-temperature thermolysis of the amino acid in specific solvents in the presence of a catalytic amount of a carbonyl-containing compound such as an aldehyde or ketone, commonly involving catalysts wherein the carbonyl group is close to (or conjugated with) an insaturation, such as a carbon-carbon double bond. (Chatelus, G. *Bull. Soc. Chim. Fr.* (1964), 2533; Hashimoto, M et al, (1986) *Chem, Lett.,* 6, 893; Wallbaum, S. et al., (1994) *J. Synth. Commun.,* 24, 1381; Hashimoto, M. et al., (1986) *Chem. Lett.* 15(6), 893-896). However, these methods can involve extreme high temperatures, long reaction times, and solvents that can withstand such temperatures, many of which are toxic or present problems with later solvent removal.

An example of a method directed at the deficiencies of traditional routes for the decarboxylation of amino acids is given by Laval and Golding (G. Laval and B. T. Golding: *One-pot sequence for the Decarboxylation of α-amino acids.* (2003). *Synlet,* 4, 542-546), where the treatment of an α-amino acid, at room temperature, with N-bromosuccinimide (NBS) in aqueous phosphate buffer at pH 5 (or in a solution of $NH_4Cl$ in ethanol/water), followed by addition of $NiCl_2 \cdot 6H_2O$ and $NaBH_4$ led to the decarboxylation—via an intermediate nitrile—to yield the corresponding amine in 59% to 81% yield (depending on the starting amino acid). Laval's method was shown to be effective in conjunction with both natural and unnatural α-amino acids, including carboxypolyamines and those amino acids decorated with other functionalities such as $CF_3$, $NHR$, $NR_2$, and $H_3C-S$ (e.g., methionine). While Laval's method is carried out in water at room temperature and pressure, it involves the use of toxic NBS and will require proper disposal of metal-, bromide- and boron-containing reaction by-products.

More recently, Zhou described a one-pot, aldehyde-induced, metal-free process for the decarboxylation of α-amino acids to synthesize N-alkyl-f-alkenyl cyclic amines with high stereoselectivity (Zhou, J. et al, (2017) *Tetrahedron Lett,* 58, 3174-3177). By varying reaction conditions, decarboxylation reactions were achieved in up to 62%. The end-products of Zhou's method, however, are not the corresponding free amines but rather N-alkyl-β-alkenyl cyclic amines.

Industrial production of amines by bio-fermentative routes (e.g., biogenic amine production by lactic acid bacteria), on the other hand, is limited to the production of naturally occurring amines and the production of amines derived from unnatural amino acids is not achieved by such means.

Thus, there is the need for an alternative method for the high-yield production and isolation of free amines that is fast, solvent-free, allows for the easy recovery of reagents, is employable in conjunction with both natural and unnatural amino acids, and provides for the recovery of useful and commercially important byproduct(s).

SUMMARY

Briefly described, the present disclosure provides methods of decarboxylation of amino acids via imine formation at elevated temperatures without the need for the addition of a solvent or performing the reaction under elevated pressure.

Embodiments of the present disclosure include solvent-free methods for decarboxylation of amino acids to produce an amine via an imine intermediate. In embodiments, the methods include the following steps:

(a) combining, in an open reaction vessel, a mixture of an amino acid and a co-reagent, the co-reagent comprising a ketone, enone, enal, aldehyde, or combination thereof, wherein the mixture does not contain a solvent;

(b) heating the mixture at about 150° C., or more, until the mixture becomes homogenous, wherein the amino acid is converted to its imine;

(c) cooling the reaction mixture from step (b) in the reaction vessel to a temperature below about 30° C.;

(d) adding an acid to the cooled reaction mixture from step (c) in the vessel; and (e) heating the acid reaction mixture from step (d) to about 50° C., or more, to hydrolyze the imine to form an amine salt.

In embodiments, the methods further include the steps of: (f) removing unreacted co-reagent or isomerized co-reagent byproduct from the reaction mixture from step (e); and (g) recovering the amine salt. In embodiments, removing unreacted co-reagent includes washing the reaction mixture with an ether solvent and water and distilling off the water, ether, and co-reagent, to recover the amine salt. In some embodiments, the method further includes combining the recovered amine salt with a base to yield the corresponding free amine.

In some embodiments, the co-reagent is a ketone, enone or enal capable of isomerization at temperatures of about 120° C., or more, to yield a byproduct selected from the group consisting of: enals, enones, phenolic terpenes, phenolic terpenoids, xylenols, and ethylmethylphenols. In some embodiments, where the amino acid does not containing acid/heat-sensitive side-chains, during step (e), the acid reaction mixture is heated to about 120° C., or more, to hydrolyze the imine to form an amine salt. In embodiments, where the amino acid does not have acid/heat-sensitive side chains and where the co-reagent is capable of isomerization at temperatures of about 120° C., or more, to yield a useful byproduct, then the reaction mixture can be heated to about 120° C., or more, to hydrolyze the imine to form an amine salt and to isomerize any unreacted co-reagent. The above methods can further comprise extracting unreacted co-reagent or isomerized byproduct; and recovering the amine salt. In embodiments, the co-reagent byproduct can be, but is not limited to, carvacrol, carvenone, thymol, xylenols, ethylmethylphenols, 2-pentenal, hex-3-en-2-one, piperitone, and 3-ethyl-6-methylcyclohex-2-en-1-one, 3-ethylcyclopent-2-ene-1-one.

The present disclosure also includes methods for decarboxylation of amino acids with acid-sensitive side chains. In embodiments, such methods include:

(a) combining, in an open reaction vessel, a mixture of an amino acid having acid-sensitive side chains and a co-reagent, the co-reagent comprising a ketone, enone, enal, aldehyde, or combination thereof, wherein the mixture does not contain a solvent;

(b) heating the mixture at about 150° C., or more, until the reaction mixture becomes homogenous, wherein the amino acid is converted to its imine;

(c) cooling the reaction mixture from step (b) in the reaction vessel to a temperature below about 30° C.;

(d) adding an acid to the cooled reaction mixture from step (c) in the vessel, after which the reaction mixture forms two layers: an organic layer comprising unreacted co-reagent and an aqueous acidic layer comprising the imine;

(e) removing the organic layer and heating the aqueous acidic layer mixture from step (d) to about 50° C., or more, to hydrolyze the imine to form an amine salt; and (f) extracting any remaining co-reagent and recovering the amine salt.

Other systems, methods, features, and advantages of the present disclosure will be or become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

Many aspects of the disclosed methods can be better understood with reference to the drawings, which are discussed in the description and examples below. The components in the drawings are not necessarily to scale, emphasis instead being placed upon clearly illustrating the relevant principles of the present disclosure.

FIG. 1 illustrates the isomerization of carvone to carvacrol in aqueous acid, which facilitates its removal from the reaction product by basic extraction.

FIG. 2 illustrates isomerizations of piperitenone or isopiperitenone to produce thymol.

DESCRIPTION

Figure 3:
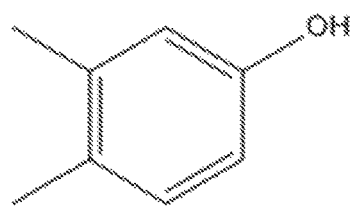
FIG. 3 illustrates chemical structures of some xylenol compounds and ethylmethylphenol compounds that can be produced as co-reagent byproducts in embodiments of the methods of the present disclosure.
Figure 3:
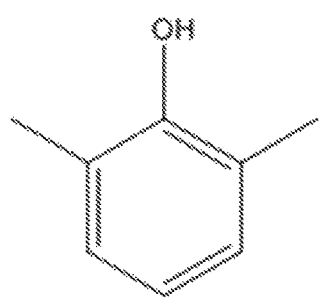
Figure 3:
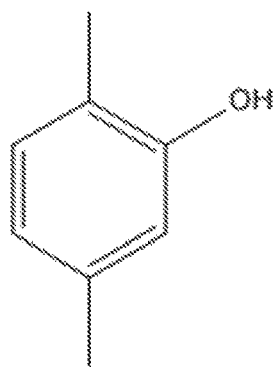
Figure 3:
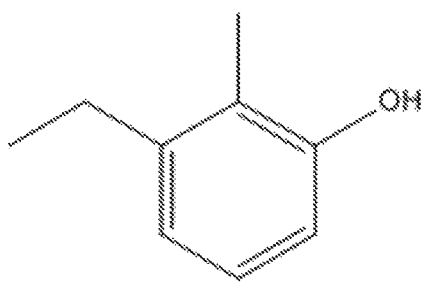
Figure 3:
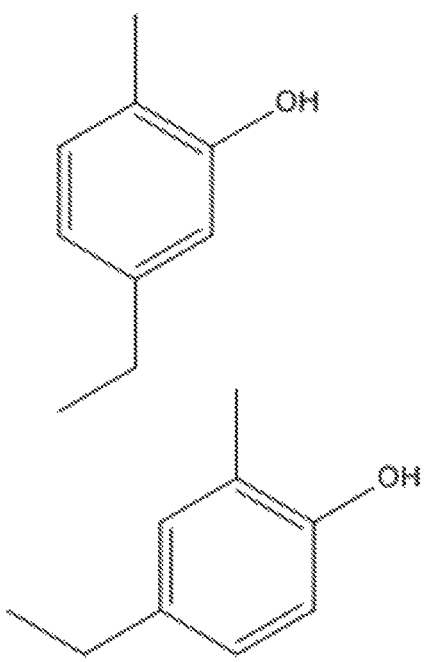

The details of some embodiments of the present disclosure are set forth in the description below. Other features, objects, and advantages of the present disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

"Room temperature" is indicates a temperature in the range of about 15° C. and 30° C. range, preferably between 15° C. and 25° C.

"Solvent free" is used herein to indicate that the reaction in embodiments of the present disclosure does not employ materials whose only function is as a medium in which to dissolve the reagents used in the method. Instead, certain reagents used in the invention also perform the function of a solvent. In some embodiments, co-reagents (which are substantially to fully recovered at the end of the reaction) may also function as the reaction medium, thus providing the function of a solvent without a separate solvent.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. Terms defined in references that are incorporated by reference do not alter definitions of terms defined in the present disclosure or should such terms be used to define terms in the present disclosure they should only be used in a manner that is inconsistent with the present disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, organic and inorganic chemistry, material science, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DISCUSSION

Embodiments of the present disclosure provide for solvent-free, low-pressure methods of decarboxylation of amino acids (including both naturally occurring amino acids and synthetic analogs) to amines (e.g., amine salts and/or free amines). In embodiments the methods also provide for concurrent production of useful byproducts. The methods of the present disclosure provide for a quick, solvent-fee, simple and effective decarboxylation of amino acids via imine formation with a co-reagent under heated conditions with consequent recovery of product amines as well as unreacted co-reagent and/or useful reagent byproducts.

Enzymatic decarboxylation of amino acids occurs in many organisms and provides a synthetic option for the decarboxylation of amino acids. Many amino acids have also been shown to undergo decarboxylation upon reflux in a high boiling solvent, such as cyclohexanol, in the presence of a ketone, such as cyclohex-2-ene-1-one or acetophenone. This is believed to occur through an active conformation of an imine intermediate. However, for synthesis of some of the more biologically relevant amines, previously reported procedures are slow and are complicated by difficult purification procedures to remove byproducts, high boiling solvents, or the need for pressurized reaction conditions.

More recently, two processes for the removal of product free amines by distillation from a high boiling solvent have been reported. These methods may assist with the problem of solvent removal for lower boiling product amines, but reaction times were still extremely long and the success of these procedures for difficult decarboxylations, such as L-histidine to histamine, are unsubstantiated and have not been reproduced. Thus, an alternative method of isolation is needed to prevent thermal degradation, especially for free amines with a high boiling point.

Recent alternative methods described in U.S. Pat. No. 9,452,954 and U.S. patent application Ser. No. 15/249,719 provide ketone/enone/aldehyde catalyst-promoted, pressurized thermal decarboxylation of amino acids to yield amines. Those methods make use of lower boiling point solvents than the conventional methods by performing the reaction under pressure with ketone/enone/aldehyde catalyst, but the solvent has to be tailored to the reaction vessel in order to not exceed the maximum pressure the vessel can withstand. Also when a microwave is used as the heat/energy source, the solvent must be chosen also based on its susceptibility to be heated by microwave radiation. Also, for all of the above methods, the solvent has to be removed after the reaction is complete. It was not previously believed to be possible to perform the reaction without the use of a separate solvent inert to the reaction and obtain the resulting amine product. For instance, as previously described by Jackson, et al. ("Rapid Conventional and Microwave-Assisted Decarboxylation of L-Histidine and Other Amino Acids via Organocatalysis with R-Carvone Under Superheated Conditions" *Synthetic Communications*, 2015, 45:23, 2691-2700, see p. 2693, first paragraph), it was discussed that reactions performed "neat" (e.g., with a catalyst but without a separate solvent) produce little to no yield.

Embodiments of the methods for decarboxylation of amino acids of the present disclosure include combining an amino acid and a co-reagent in a vessel to form a mixture. In embodiments, the solvent-free methods of decarboxylation of amino acids according to the present disclosure are carried out in open reaction vessels that allow for immediate elimination of gaseous reaction by-products (e.g., $CO_2$). Embodiments of the methods of the present disclosure include combining a mixture of an amino acid and a co-reagent, co-reagent is a ketone, enone, enal, or aldehyde, or mixture thereof, without a separate solvent. In these embodiments, the co-reagent, which is liquid at the reaction temperatures, functions both as a co-reagent as well as the medium for the reaction.

The above mixture is heated at about 150° C. to 200° C., or more. During the process, the heterogeneous mixture becomes homogenous as the reaction proceeds and carbon dioxide gas is released during decarboxylation and the amino acid is converted to its corresponding imine intermediate. Thus, the progression of the reaction can be monitored via the release of carbon dioxide gas as well as by noting the homogeneity of the reaction mixture. Thus, in embodiments, the mixture is heated until the mixture becomes homogeneous. In embodiments, the mixture is heated for about 5 to 60 minutes, or longer, such that the amino acid is converted to its imine. In embodiments, the mixture is heated at a temperature of at least about 180° C. (e.g., about 180° C., or more) for at least 5 minutes, or more. The resulting reaction mixture in the vessel includes the imine, any unreacted co-reagent, and any unreacted amino acid. If the reaction is not complete (in embodiments, a complete reaction is indicated by the reaction mixture turning from a heterogeneous slurry into a transparent/homogeneous liquid), additional heating is performed, as described below.

Various co-reagents can be used in the methods of the present disclosure and can function as both reagent and reaction medium. Some examples of co-reagents that can be used in the methods of the present disclosure include, but are not limited to, ketone, enone, enal, and/or aldehyde including, but not limited to, cyclohex-2-ene-1-one, acetophenone, 3-penten-2-one, butanone, dihydrocarvone, R-carvone, S-carvone, β-ionone, R-pulegone, 3-methylcyclohex-2-enone, carvenone, citral, piperitone, piperitenone, isopiperitenone, methyl vinyl ketone, butenones, acetone, cinnamaldehyde, pentadione, 2-phenylpropenal (CAS 4432-63-7), and other β-ene-aldehydes.

In embodiments, the co-reagent is an enone or enal capable of isomerization (e.g., at temperatures of about 180° C., or more) to yield a phenolic terpene or phenolic terpenoid byproduct. In embodiments, the co-reagent is an alpha, beta-unsaturated ketone. In embodiments, the co-reagent is an enone. In embodiments enone co-reagents can include enones such as, but not limited to, R-carvone, S-carvone, citral, 3-penten-2-one, cyclohex-2-ene-1-one, β-ionone, R-pulegone, carvenone, piperitenone, isopiperitenone, and 3-methylcyclohex-2-enone. In embodiments of the present disclosure, the co-reagent is carvone (m.p.: 77.4° C., b.p.: 447.8° C.) (R- or S-carvone or combination), or dihydrocarvone (m.p: 11° C., b.p.: 221° C.). In embodiments, the co-reagent is an enal such as cinnamaldehyde or 2-enepropanal. In the methods of the present disclosure carvones and β-ene-aldehydes are the preferred co-reagents and also function as reaction mediums and decarboxylation reagents.

As described in more detail below, in some embodiments, the co-reagent used in the methods of the present disclosure can also lead to useful byproducts that can later be recovered and isolated for other purposes. In some embodiments, the co-reagent isomerizes during decarboxylation reaction at higher temperatures to produce a useful byproduct. Some such isomerized co-reagent byproducts have commercial importance, and the methods of the present disclosure provide efficient production of such byproducts.

For instance, carvone isomerizes to carvacrol due to keto-enol tautomerism and acid-catalyzed alkene migration, driven by the stability of the resulting aromatic system. Carvacrol is a monoterpenoid phenol with odor of oregano and is used for many commercial purposes. Similarly, the ketone co-reagent dihydrocarvone also isomerizes undergoing acid catalyzed alkene migration similar to carvone resulting in the alpha, beta-unsaturated enone carvenone. Carvenone is thus also a useful co-reagent byproduct that can, itself, be used as a co-reagent for the decarboxylation process of the present disclosure. It is relevant to note, for example, limonene, another commodity used in the food, nutritional supplements and cosmetic industries can be produced from carvacrol, a byproduct of the invention.

Other enone co-reagents, such as piperitenone, isopiperitenone, can isomerize to produce thymols. Other phenolic terpenes and terpenoids, other phenolic structures (such as, but not limited to xylenols and ethylmethylphenols), and other acyclic and cyclic enal and enone analogs of carvenone (such as, but not limited to 2-pentenal, hex-3-en-2-one, piperitone and 3-ethylcylcopent-2-ene-1-one) can be produced good yields in the methods of the present disclosure as byproducts from suitable enone and or ketone precursors/co-reagents. The structural features and reaction conditions appropriate for isomerization are discussed in greater detail in the Examples below.

In some embodiments, enone and/or enal co-reagents, cyclohexanone, acetophenone and other aryl-substituted aldehydes, may not undergo isomerization and remain in their original forms during the reaction and would be removed at the end of the reaction for later re-use.

In an embodiment, use of the enones R- or S-carvone in methods of the present disclosure for decarboxylation of amino acids leads to the formation of carvacrol as a byproduct. Carvacrol, a component of oil of oregano, is a useful volatile compound that can be recovered and used in the flavoring industry as well as other uses. In other embodiments, use of the ketone dihydrocarvone as co-reagent leads to the formation of carvenone as byproduct. Carvenone can also be used as a co-reagent in the methods of the present disclosure. In embodiments, such byproducts can be recovered as described below. In embodiments, the co-reagents piperitenone or isopiperitenone can be used as co-reagents for the decarboxylation and can isomerize to produce thymol.

As described in the examples below, the load of the co-reagent is a factor affecting the reaction rate and ease of purification. It was found in some embodiments that about 4 mole equivalents of co-reagent (e.g., carvone) produced an appreciable catalytic effect and also eliminated the need to use a separate, inert solvent. Thus, in embodiments, the mixture includes from about 2 to about 10 mole equivalents of co-reagent, in some embodiments about 3 to about 5 mole equivalents are used.

In preferred embodiments of the invention, carvone or a derivative of carvone that is liquid at the temperature at which the decarboxylation reaction is carried out, is used in a large (200% to 900%, preferably between 300% and 500%) molar excess and acts as co-reagent as well as the reaction medium (or melt, or flux). This strategy eliminates the need for a separate reaction solvent, reduces the number of purification steps needed to obtain the desired amine, increases the product yield and enables low-pressure reactions for the decarboxylation of amino acids. In this case, the reaction intermediate is preferably the iminium salt derived from the amino acid, rather than free imine. However, for simplicity, the description of the method herein will allude to "imine" (rather than "iminium salt") formation as the intermediary step.

In the methods of the present disclosure, the heating steps can be performed in a microwave or, alternatively, in traditional oil bath. In some embodiments using the oil bath for heating, the oil can be, but is not limited to, silicone oil. In embodiments, the initial mixture of amino acid and co-reagent is heated in a microwave to a temperature of about 180° C. to about 190° C. for about 5 min to about 60 min, or until the reaction mixture becomes homogeneous or other indication of reaction completion. In embodiments, a microwave reactor with a thermometer and automatic feedback loop is used to maintain the temperature. After the initial heating, if the reaction mixture is not complete (e.g., not homogeneous/clear, no color change, still producing carbon dioxide gas, or other criteria, as applicable) a second heating step can be conducted. In embodiments, the mixture can be re-heated in the microwave to about 190° C. for about 5 to about 30 min longer.

When an oil bath is used, additional heating time may be needed, since it is more difficult to maintain a constant heat in the oil bath and the temperature of the reaction medium is generally not homogeneous. In embodiments, the initial mixture of amino acid and co-reagent is heated in an oil bath at a temperature of about 180° C. to about 190° C. for about 30 min to about 60 min. In embodiments, if the reaction is not complete after the first heating, an additional heating can be conducted, such as by heating again at about 180° C. to about 190° C. for about 30 to about 60 min longer. To account for changes in temperature of the oil bath when the room temperature reaction vessel is added, the oil bath may be heated to a higher temperature prior to addition of the reaction vessel. For instance, in embodiments, the oil bath is heated to a temperature of about 210° C. prior to addition of the reaction vessel and brought back to a temperature between about 185° C. to about 190° C. after addition of the reaction vessel. This effect is mitigated by increasingly large bath volume. Other heating sources (e.g., infrared radiation) can also be used instead of oil bath or microwave.

After the initial heating step, the amino acid will be substantially converted to its imine. To achieve high yield of amine from the imine, a hydrolysis step can be added. Hydrolysis can be achieved by heating in an acid (e.g., a dilute acid). Acids, such as, but not limited to HCl, can be used in the methods of the present disclosure. In embodiments, the methods include cooling the reaction vessel to a temperature below about 30° C. (e.g., about 15° C. to 30° C.). In embodiments the vessel is cooled to about room temperature. After cooling, embodiments of the methods of the present disclosure include adding an acid to the reaction mixture in the vessel, and subsequently heating the acid reaction mixture to hydrolyze the imine to form an amine.

The addition of aqueous acid with heat converts the imine intermediate into co-reagent and the decarboxylated amine salt. The uncoupling of the carvone and amine salt occurs at about 50-60° C., so in embodiments the acid reaction mixture is heated to a temperature of at least about 50° C. In embodiments the mixture is heated for a time period of about 25 min to about 60 min. In embodiments, it is heated for about 30 min. In embodiments, after addition of the acid, the reaction vessel is closed for the heating step. In embodiments the acid reaction mixture is heated to a temperature of about 50-200° C., depending on the nature of the amino acid.

In embodiments, the acid heating is done at a temperature range of about 50° C.-75° C. or about 180° C.-200° C., which range may depend on the amino acid being decarboxylated. The temperature used for the acid hydrolysis may be modified depending on the starting amino acid. For instance, certain amino acids, such as glutamine and asparagine have side chains that are sensitive to high temperature acid hydrolysis. Thus, in embodiments, to preserve side chain integrity for such amino acids, a lower temperature acid hydrolysis at about 50° C.-75° C. is used. In other embodiments, lower temperatures are not needed and higher temperature hydrolysis may be employed, which can perform the hydrolysis simultaneously with isomerization of unreacted co-reagent to produce co-reagent byproducts, if desired.

In some embodiments, particularly where it is not desired to isomerize the co-reagent, the co-reagent can be separated before or after heating, or at both stages. When acid is added to the imine reaction mixture, even before heating, the mixture forms two layers, a top organic layer, which includes primarily co-reagent, and a lower aqueous layer including the iminium salt, which will be converted to the corresponding amine salt upon heat. Thus, if desired, some of the organic layer including co-reagent can be separated before the heating step, and, in embodiments, additional co-reagent can be recovered after the formation of the amine salt by extracting the aqueous solution with an extraction solvent such as ethyl ether. This method is useful in embodiments where lower temperature hydrolysis is used (such as for preservation of sensitive side chains).

Thus, in embodiments, reaction temperature and time are optimized based on structural features of, and sensitivity to, aqueous acid by the starting amino acids. In contrast to embodiments where the amino acid has sensitive sidechains, when the amino acid does not contain side-chains that are sensitive to acid hydrolysis, after addition of the acid, the reaction mixture can be heated at a higher temperature, such as about 180° C.-200° C. to simultaneously convert the imine to the amine salt and isomerize certain co-reagent to the above-mentioned byproducts.

For purposes of illustration of differences between embodiments of methods involving sensitive vs. non-sensitive amino acid side chains, the following embodiments will be described with the use of R-carvone and certain specific parameters (temperature, mol equivalents, identity of acid, etc.). It is understood that these are provided for purposes of illustration only and are not intended to be limiting. In an example embodiment where the starting amino acid does not contain side chains sensitive to aqueous acid (e.g., isoleucine), 1 mol equivalent of amino acid and 2 to 10 (preferably 3-5) mol equivalent of R-carvone are mixed in an open vessel and the mixture is heated at 180° C.-190° C. for about 1 hour, after which time the solution is allowed to cool down to a temperature below 30° C. Then, 2 to 4 (preferably 2) mol equivalent of HCl (from a 2M solution) are added, with moderate stirring, to the vessel, which is then closed and again heated at 180° C.-190° C. for about 30 minutes and again allowed to cool down to room temperature to yield a two-phase solution. The aqueous layer contains the amine product present as in the form of an organic ammonium chloride and can be extracted therefrom and purified by traditional processes. The organic layer yields carvacrol (>99%), and the free amine salt can be recovered from the aqueous layer. In other certain embodiments, when the starting amino acid does contain side chains that are sensitive to aqueous acid (e.g., glutamine and asparagine), the process can be similar to that described above with initial mixing and heating of amino acid and carvone, except that, after the first addition of 2 mol equivalent of HCl, two distinct layers are formed and the top organic layer (containing carvone) is removed. The remaining aqueous layer, which contains the acid and imine intermediate, is heated at 60° C. to 80° C. for about 30-60 min in a closed vessel, to yield the desired amine as an ammonium salt.

In some embodiments, greater purity of amine product is possible if the acid heating step is conducted at higher temperatures, such as above about 180° C., to isomerize the co-reagent, as described above, during the hydrolysis of the imine with acid. In embodiments, the acid is HCl. In embodiments the acid is 2M HCl. In some embodiments, such as when the products and/or amino acids are sensitive to acid during hydrolysis at 180° C., hydrolysis at 80° C. with soxhlet extraction, for removal of co-reagent, can be performed instead.

Additionally, whether the organic phase containing co-reagent and/or isomerization byproduct is separated/discarded before or after the acid heating step, in embodiments, remaining co-reagent and/or byproduct can be recovered from the reaction mixture after the hydrolysis step by extraction by washing with water and extraction solvent (e.g., ether solvent such as, but not limited to diethyl ether) as described above, and the amine salt can be recovered.

In some embodiments, when the co-reagent can be isomerized to a useful byproduct, but high temperature hydrolysis is not desired, isomerization can be done after extracting the co-reagent. For instance, in embodiments, remaining unreacted carvone can be isomerized to carvacrol by heating at a temperature of about 180° C., or more (e.g., about 185° C. or more, about 190° C., or more, etc.), for about 5 min, or longer. While some other ketone, enone, and aldehyde co-reagents in addition to carvone, for example dihydrocarvone, isomerize in acidic reaction conditions at temperatures above about 120° C. or above about 180° C. (or other intermediate range, e.g., between about 120° C. and about 180° C.), as described above, other co-reagents remain in their original form (even after heating to over 180° C. in acid) and must be recovered via isolation/purification methods such as extraction with diethyl ether. Isomerization of R-Carvone and S-Carvone to carvacrol is advantageous due to its ability to drive the hydrolysis equilibrium.

As discussed, co-reagents and co-reagent byproducts can be recovered from the reaction mixture (before or after hydrolysis to the amine salt) by traditional methods such as, for example, by washing with water and organic extraction solvent (e.g. an ethyl solvent, such as, but not limited to, diethyl ether). Co-reagents and co-reagent byproducts (e.g., carvacrol, carvenone, piperitone, etc.) may also be isolated and/or further purified via other means, such as distillation, known to those of skill in the art.

The corresponding or ammonium salt (e.g., amine hydrochloride) can be recovered by distilling off the solvent and/or water or the product crystalized from aqueous solutions, if so desired. The washing and distillation step can be repeated as necessary. In embodiments the reaction mixture is washed three times with ether and water solvent. In embodiments, after washing and distilling off the water and solvent, the amine salt can be dried (e.g., in an oven). In the aqueous layer can be dried on a rotovap at about 0 until dry to provide the ammonium chloride salt of the decarboxylated amino acid. The salt can then be recrystallized from diglyme.

The above methods of the present disclosure can be conducted with any amino acids where it is desirable to convert the amino acid to the corresponding amine. Some exemplary amino acids that can be used in the methods of the present disclosure include, but are not limited to, isoleucine, phenylalanine, tryptophan, tyrosine, glycine, alanine, valine, proline, leucine, threonine, histidine, lysine, glutamine, asparagine and other aminoacids, including artificial ones, such as, for example, N-methyl amino acids and ring-substituted phenylalanine and tyrosine derivatives. Amino acids suitable for decarboxylation according to the methods of the present disclosure also include synthetic amino acids and other non-naturally occurring amino acid analogs.

In accordance with standard nomenclature, amino acid residues are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). As used herein the term "amino acid" refers to either natural and/or unnatural or synthetic amino acids, including glycine and both the D or L optical isomers, cyclopropyl-, cyclobutyl-, cyclopentyl- and cyclohexyl-containing synthetic amino acids, and amino acid analogs and peptidomimetics.

As described in the examples below, in embodiments of the present disclosure methods of rapid decarboxylation of Isoleucine (Ile) and other L-amino acids have been accomplished via stable imine formation with R-carvone, and other co-reagents, with subsequent one-pot hydrolysis under heated conditions using both conventional heating and microwave radiation. The entire conversion from amino acid to amine hydrochloride or dihydrochloride salt, as appropriate, was accomplished in about 3 hours or less in all cases, followed by drying with isolated yields of 50-90%.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure (STP) are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

Now having described the embodiments of the disclosure, in general, the following examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

EXAMPLES

The following examples describe decarboxylation of natural L-amino acids via imine formation with R-carvone and other co-reagents with subsequent one-pot hydrolysis under superheated conditions using both conventional heating and microwave radiation. Reaction yields, based on amounts of amine produced relative to the starting amount of amino acid, are similar to those described in U.S. Pat. No. 9,452,954 and U.S. patent application Ser. No. 15/249,719, and are in the 40% to 99% range.

Example 1—General Solvent-Free Decarboxylation of Amino Acids Via Imine Intermediate This example describes decarboxylation of various amino acids using the methods described above with R-carvone and other co-reagents. Decarboxylation was more rapid (5-60 min) than previous methods as the reaction vessels were heated to 180° C. for 5-10 min. Approximately 80% of the R-carvone could be recovered via extraction with diethyl ether when the hydrolysis was conducted at 80° C. To obtain a higher purity product with non-sensitive amino acids, a high temperature hydrolysis was conducted to isomerize residual R-carvone to carvacrol. Isolated yields of amine hydrochloride salts were comparable or improved over previous methods ranging from 60-90%. Products were characterized and their purity assessed, primarily via GC/MS. Given the exceptionally clean $^1$H NMR spectra and simplicity of the procedure, purity of hydrochloride salts was estimated to be >99% by $^1$H NMR.

Materials and Methods 5 mmol scale microwave experiments were performed in open reaction vessels inside the Milestone Start SYNTH microwave oven with external infrared temperature control. Traditional heating experiments were performed in silicone oil in the same reaction vessels. Reagents were purchased from Sigma-Aldrich and used without additional purification. All amines were characterized by GC/MS and data compared with known spectra from the literature.

General "One-Pot" Procedure for the Decarboxylation of Amino Acids

A magnetic stir bar, 10 mmol of R-Carvone, and 5 mmol of amino acid were charged to a reaction vessel. The vessel was heated from room temperature to 180° C. over 5 min (preferably at about 60 minutes) with stirring. If necessary the reaction vessel was maintained at 180° C. for additional time until the slurry became clear. The vessel was allowed to cool to room temperature and 10 mL of 2M HCl was added. The vessel was heated to 180° C. for an additional 20 min with stirring and allowed to cool. The aqueous reaction mixture was washed three times with 25 mL of ether and then the aqueous phase was evaporated in a rotovap to near complete dryness and the remaining solution kept under vacuum, at 60° C. to yield anhydrous amine hydrochloride. The hydrochloride salt was transferred to a vacuum oven and dried overnight at 60° C. The hydrochloride salt can be purified by recrystallization or by washing with non-polar solvents, or other methods generally known and accepted by a reasonably skilled practitioner. The hydrochloride salt was then weighed and analyzed via GC/MS, IR and NMR, confirming identity and purity.

Example 2—Solvent-Free, Low-Pressure Method for Producing Amines from Amino Acids, when the Parent Amino Acid does not Contain Side Chains that are Sensitive to Acid Hydrolysis One (1) mol equivalent of amino acid (e.g., isoleucine) and 4 mol equivalents of R-Carvone are stirred in an open vessel at 185° C. for 1 hour. Over the course of heating the heterogeneous mixture becomes homogeneous. The vessel and contents are removed from heat and allowed to cool to room temp. 2 mol equivalents of HCl (from a 2M solution) are added to the vessel. The vessel is closed and heated to 185° C. for 30 minutes. The vessel and contents are removed from heat and allowed to cool to room temperature. The vessel contents form two distinct layers which are separated in a separatory funnel. The top organic layer contains Carvacrol (>99%). The aqueous layer is extracted three times with 10-mL of ethyl ether and the ether extracts are combined with the organic layer. The aqueous layer is dried on a rotovap at 60° C. until dry to give the ammonium chloride salt of the decarboxylated amino acid. The ammonium chloride salt of the target amine (e.g., 2-methyl-n-butylamine) is recrystallized from diglyme in high yields.

Example 3—Solvent-Free, Low-Pressure Method for Producing Amines from Amino Acids, when the Parent Amino Acid Contains Side Chains that are Sensitive to Acid Hydrolysis 1 mol equivalent of amino acid and 4 mol equivalents of R-Carvone are stirred in an open vessel at 185° C. for 1 hour. Over the course of heating the heterogeneous mixture becomes homogeneous. The vessel and contents are removed from heat and allowed to cool to room temp. 2 mol equivalents of 2M HCl are added to the vessel forming two distinct layers. The top organic layer, comprised primarily of R-Carvone, is removed. The vessel containing a heterogeneous aqueous solution of the iminium salt is closed and heated to 60° C. for 30-35 minutes. The vessel and contents are removed from heat and allowed to cool to room temperature. The aqueous solution is extracted at least three times with 10-mL of ethyl ether to remove R-Carvone and Carvacrol. The aqueous solution is dried on a rotovap at 60° C. until dry to give the ammonium chloride salt of the decarboxylated amino acid. The ammonium chloride salt is recrystallized from diglyme.

Example 4—Results and Discussion from Ex. 1-3

Addressing the problem of long reaction times required for the decarboxylation of many amino acids such as histidine (>40 hrs) using extant procedures, it was previously envisioned that chemistry at temperatures above the reflux temperature of cyclohexanol (~160° C.) may provide a solution. However, in earlier efforts a significant amount of effort had been devoted to the removal of cyclohexanol and other high boiling solvents at the expense of yield and efficiency. An advantage to using a nonpolar alcohol, such as cylcohexanol, as solvent was the solubility of the amine product and insolubility of amino acids, thus allowing for visual determination of reaction completion (from slurry to clear solution). Rather than employing a solvent, such as a higher boiling solvent system, which would yield the same difficulties as seen in the conventional methods, or the use of a pressurized reaction system using a solvent with a lower normal boiling point, the above examples of the present disclosure eliminate the solvent during the imine formation altogether.

Both microwave promoted and hot oil bath systems were investigated. The identity and load of the co-reagent was also a factor to consider that can affect the reaction rate and overall ease of purification of the product mixture. In conventional methods, a 1% v/v of cyclohex-2-ene-1-one (2) has been reported for histidine decarboxylation; however, others have reported difficulty in repeating these results without a substantially higher catalyst load. Significant impurities were also observed in the resulting reaction mixture by those authors, and in later attempts to reproduce the experiments. Others alternatively used acetophenone to modest success for the decarboxylation of histamine at 20 mol % in >40 hr. It was postulated that the greater the stability of the imine, the greater the reaction rate at a given co-reagent load, and, indeed, cyclohex-2-ene-1-one proved to provide a greater catalytic effect at 20 mol % than acetophenone. On a belief that the enone functionality of cyclohex-2-ene-1-one provides some advantage over the benzyl ketone and, given its toxicity and expense, an alternative was selected for testing in the present examples. As shown in Scheme 1, illustrated in FIG. 1, R-carvone (3), the natural product of spearmint oil, was selected for its potential to retain the catalytic advantage over acetophenone while providing an alternative method of removal of the co-reagent based on the isomerization reaction of R-carvone (3) to carvacrol (4).

It was also observed during these experiments that the rate of reaction significantly increased at the higher co-reagent load, an effect maximizing at about 2 mole equivalents for both cyclo-hex-2-ene-1-one (2) and R-carvone (3). The reaction times of a series of microwave assisted decarboxylations of phenylalanine in n-propanol at 190° C., were set at 30-60 min.

Data previously included in U.S. Pat. No. 9,452,954 and application Ser. No. 15/249,719, compared several catalysts at the 2 equivalent load for performance on a series of decarboxylations in a solvent-based, high-pressure system. Results led to the choice of carvones as co-reagents for the method described herein. R-carvone, an inexpensive, readily available alpha unsaturated ketone natural product, was selected. The isomerization reaction of carvone produces carvacrol (FIG. 1), a phenolic natural product that would be inert to the product amine and is also a useful compound that can be recovered for other uses (e.g., oil of oregano), as described in greater detail in Example 5 below.

Considering that the reaction is thought to occur through a carboxylic acid imine intermediate and given the observed rise in impurities as a result of increasing the catalyst load from the Hashimoto procedure, the fate of the decarboxylated imine was then investigated as follows. A large excess of carvone was added to the reaction mixture to attempt to capture all product amine as an imine with carvone. The imine was then transferred into an aqueous acid mixture, excess carvone removed via ether wash, and then returned to an organic phase via neutralization with NaOH solution. A significant degree of hydrolysis was expected; however, in these observations, the imine of the decarboxylated product was quite stable and persisted as demonstrated by the GC-MS spectrum and gas chromatograph of the product mixture of decarboxylated phenylalanine.

It was observed that only after heating in acid at >50° C. did the hydrolysis occur. Even after one pot reflux with many times the reaction volume of 2.0 M HCl, it proved difficult to adequately remove all traces of the imine at system equilibrium. Each conventional method of amino acid decarboxylation fails to account for the quantity of imine that may remain, thus lowering the yield and purity of the crude product and leading to further purification.

Previously, it was envisioned that the complete hydrolysis of the imine could be accomplished via the removal of the catalyst in situ. If a low boiling ketone, such as acetone, or other aldehyde catalyst were used, it would be sealed in the pressurized vessel during decarboxylation and then distilled away from the product mixture during imine hydrolysis. Several decarboxylations were accomplished using acetone as catalyst but they were not efficient.

Using R-carvone as catalyst (in the solvent-based process, as previously described), a 5 min reflux at 180° C. in 2 M HCl hydrolyzed the imine and isomerized carvone to carvacrol. The carvacrol was then easily removed via ether extraction. It should be noted that gentle reflux at 80° C. allows the imine to hydrolyze in equilibrium, and ~80% of the carvone catalyst may be recovered via three sequential refluxes and extractions. If the carvone is recovered in this way, a final high temperature reflux can be performed to isomerize residual carvone to carvacrol for isolation of amine hydrochloride salt of highest purity.

In the present examples it was examine whether carvone could function as both co-reagent and reaction medium in the decarboxylation of amino acids carried out in open vessels, thus eliminating the need for high pressures and a foreign solvent. As shown in examples 2 and 3 above, this method provide successful and the new method led to a much simpler, cleaner, and safer process for the production of amines.

Example 5-Carvone to Carvacrol Conversion and Isolation in Organocatalytic Decarboxylation of Amino Acids This example provides experimental evidence concerning the optional conversion of an enone decarboxylation co-reagent, carvone, to useful byproduct carvacrol, the phenolic oil of oregano, and recovery of this formed essential oil. Additionally, this conversion efficiently drives the conversion of imine decarboxylation intermediate species to product free amine described in the examples above.

Such a conversion of the co-reagent to a useful byproduct is unique to co-reagents with potential for structural rearrangement forming an aromatic phenol ring. The carvone "R" and "S" stereoisomers have an exocyclic unsaturation, which is incorporated into the ring in acidic conditions causing a net conversion of enone to phenol functionality, as illustrated below. Only cyclic enones exist in natural equilibrium with enol tautomers with extended conjugated electron systems that invite isomerization. The exocyclic unsaturation migrates to the ring in acidic conditions to form the highly stable phenolic system. Carvone is a cheaply available natural oil fitting the criteria of cyclic enone with the exocyclic unsaturation.

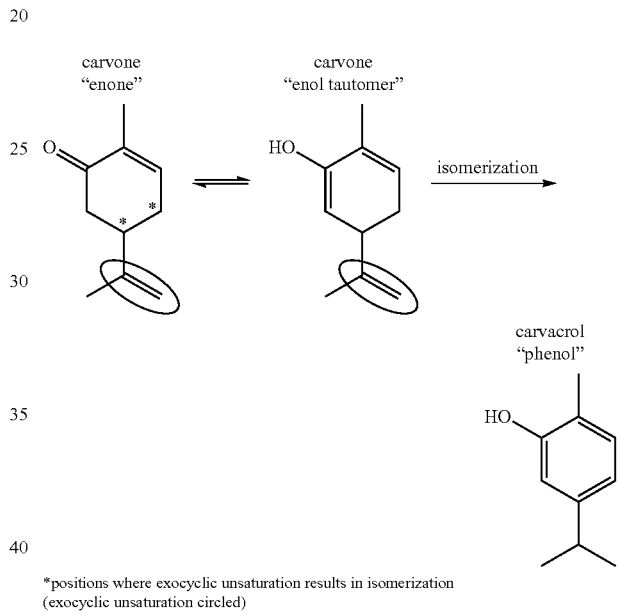

*positions where exocyclic unsaturation results in isomerization (exocyclic unsaturation circled)

In general, enone and ketone co-reagents, which lack one or both of these criteria, will also catalyze decarboxylation on amino acids as described above, but must be removed in several purification steps and are not isomerized in such a way as the cyclic enones.

Methods and Results

To illustrate generality of this conversion, several structurally diverse amino acids (Ile, Phe, Hios, Gln and Asn) were decarboxylated and isolated according to the methods described in Examples 2 or 3 above, as applicable but with careful attention to purity and yield of carvacrol rather than recovery of carvone co-reagent. In all cases, carvacrol yield is above 97% and excess carvone can be recovered quantitatively.

If desired, instead of recovering carvone after the first hydrolysis step, carvone may be isomerized to useful byproduct carvacrol by conducting acidic aqueous hydrolysis at higher temperatures (e.g., temperatures above about 180° C.). Not only does the conversion drive the process to greater yield and purity of the product amine, but also generates the oil of oregano (carvacrol) byproduct.

Additionally, if desired, the imine of most decarboxylation products may be stored over 3 angstrom molecular sieves, rather than hydrolyzing the imine in aqueous acid. The imines are stable when stored in this solution at room temperature.

Example 6—Additional Enone Co-Reagents for Decarboxylation of Amino Acids

This example describes methods for the use of various enone co-reagents in the solvent-based, pressurized decarboxylation of amino acids such as in the methods described in U.S. Pat. No. 9,452,954 and application Ser. No. 15/249,719, incorporated by reference herein. Evidence of the imine intermediate of each decarboxylation in those applications, as well as the purity of the recovered catalysts was demonstrated via GC-MS data, and purity of the recovered product amine hydrochloride salts was shown via HNMR data. In general, decarboxylation rates of the enones were similar to carvone, achieving elimination of carbon dioxide in less than 5 min as the reaction vessel is heated to 180° C. It is believed that these enones can be used as co-reagent in the solvent-free methods of the present disclosure.

Methods

Figure 4:
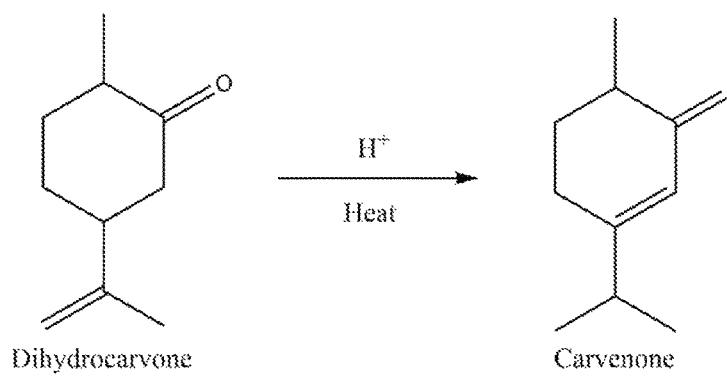
FIG. 4 illustrates acyclic and cyclic enal and enone analogs of carvenone (such as 2-pentenal, hex-3-en-2-one, piperitone, 3-ethyl-6-methylcyclohex-2-en-1-one, and 3-ethylcyclopent-2-ene-1-one) that can also be produced as co-reagent byproducts in embodiments of methods of the present disclosure.
Figure 4:
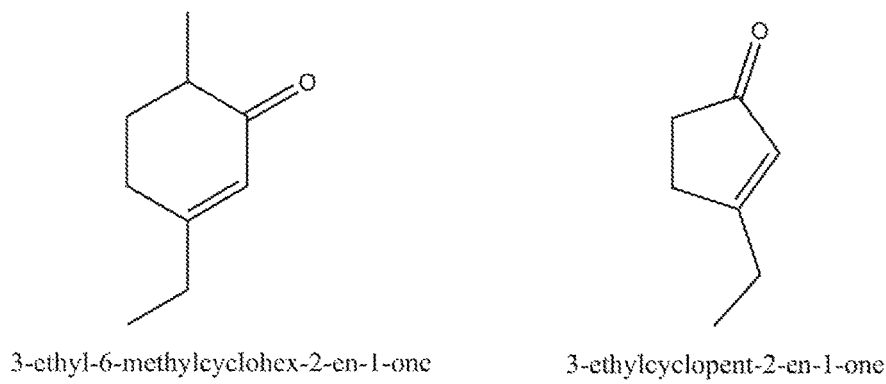
Figure 4:
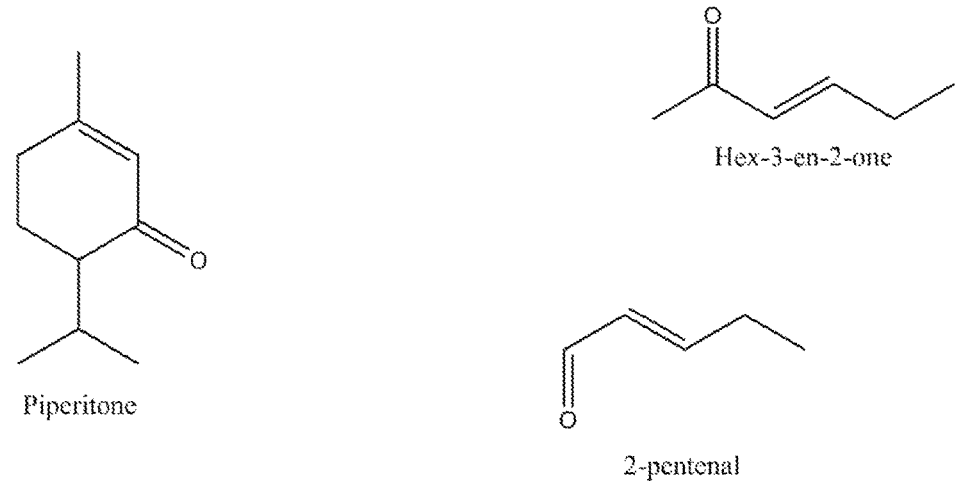

To illustrate use of multiple enone catalysis in the methods of the present disclosure for decarboxylation of amino acids, the enones citral, α-ionone, β-ionone, R-pulegone, verbenone, and 3-methylcyclohex-2-enone can be used as co-reagents in the decarboxylation of phenylalanine according to the procedures described above in Example 1. Additionally, the ketone dihydrocarvone given its structural similarities to carvone and known isomerization reaction to the enone, carvenone can also be used. Carvenone serves as an effective co-reagent and useful byproduct. The structures of the enone co-reagents are shown below, with carvone structure provided as reference, and some are shown in FIGS. 3 and 4. Results of the previous experiments with citral, α-ionone, β-ionone, R-pulegone, verbenone, 3-methylcyclohex-2-enone, dihydrocarvone, and R-carvone were presented in Table 4 of application Ser. No. 15/249,719.

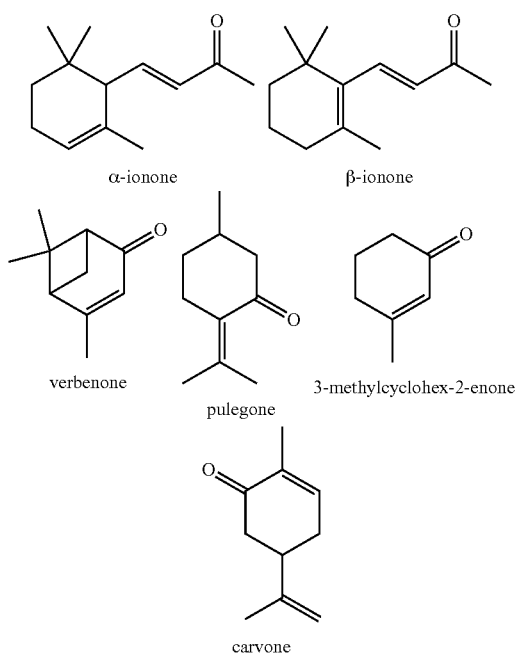

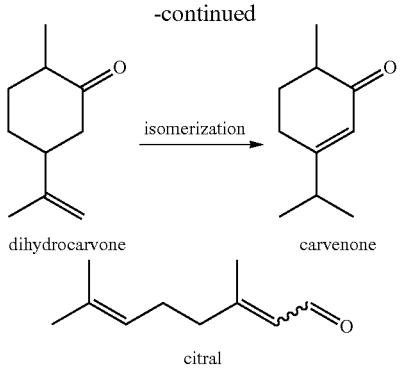

In the methods of the present disclosure, hydrolysis of the imine intermediates to product amine hydrochloride salts proceeds as with R-carvone in Examples 1, 2 and 3. Heating to a temperature of about 60-80° C. in aqueous HCl facilitates hydrolysis of imines. Co-reagents partition with the aqueous layer and can be recovered neat or extracted with a typical organic extraction solvent with a couple of exceptions. Dihydrocarvone isomerizes to carvenone, a more stable enone, during hydrolysis, as illustrated in FIG. 4 (similar to isomerization of carvone/carvacrol described in Example 2, above). The carvenone recovered is also ideally suited for the decarboxylation process and should be considered a useful byproduct.

CONCLUSION

The data presented in the present example support the broad efficacy of metal-free enone catalysis for the decarboxylation of amino acids at low pressures, in the absence of an added solvent and under relatively mild conditions. Carvone has the ability to isomerize in such a way (enone to phenol) that drives the imine hydrolysis equilibrium to completion resulting in the highest initial purity (>99%) of product hydrochloride salts Dihydrocarvone, which has been previously shown to be an efficient catalyst, also shows the ability to isomerize to a useful by-product, which can be recovered in good yield.

Other enone and/or ketone co-reagents not tested in the present example can also have the ability to isomerize similar to dihydrocarvone and carvone to produce a useful byproduct. Such co-reagents include enones such as piperitenone or isopiperitenone, which can isomerize to phenolic terpenes (such as thymol, see FIG. 2) and/or phenolic terpenoids. Other appropriate enone, enal, and/or ketone co-reagents can isomerize to produce other phenolic terpenes and terpenoids, other phenolic structures, such as, but not limited to xylenols and ethylmethylphenols (see FIG. 3), and other acyclic and cyclic enals and enones, such as, but not limited to 2-pentenal, hex-3-en-2-one, piperitone, 3-ethyl-6-methylcyclohex-2-en-1-one, and 3-ethylcyclopent-2-ene-1-one (see FIG. 4).

REFERENCES

1. Galat, A.; Friedman, H. L. *J. Am. Chem. Soc.* 1949. 71, 3976.
2. Hashimoto, M.; Eda, Y.; Osani, Y.; Iwai, T.; Aoki, S. *Chem. Lett.* 1986, 6, 893.
3. Yeh, W. L. et al.; 2002. U.S. Pat. No. 6,403,806 BI.
4. Martins, C. P. B., et al. *J. Chromatogr. A.* 2008, 1210, 115.
5. Omeis, M., et al. 2008. U.S. Pat. No. 7,485,756

6. Yaegashi, K., et al., 2009, EPO Patent: EP1586553
7. Chatelus, G. Bull. Soc. Chim. Fr. (1964), 2533
8. Wallbaum, S. et al., (1994), J. Synth. Commun., 24, 1381
9. G. Laval and B. T. Golding: One-pot sequence for the Decarboxylation of α-amino acids. (2003). Synlet, 4, 542-546,
10. Zhou, J. et al, (2017) Tetrahedron Lett, 58, 3174-3177

The invention claimed is:

1. A solvent-free method for decarboxylation of amino acids to produce an amine via an imine intermediate, the method comprising:
   (a) combining, in an open reaction vessel, a mixture of an amino acid and a co-reagent, the co-reagent comprising a ketone, enone, enal, aldehyde, or combination thereof, wherein the mixture does not contain a solvent;
   (b) heating the mixture at about 150° C., or more, until the mixture becomes homogenous, wherein the amino acid is converted to its imine;
   (c) cooling the reaction mixture from step (b) in the reaction vessel to a temperature below about 30° C.;
   (d) adding an acid to the cooled reaction mixture from step (c) in the vessel; and
   (e) heating the acid reaction mixture from step (d) to about 50° C., or more, to hydrolyze the imine to form an amine salt.

2. The method of claim 1, wherein the reaction vessel is closed during step (e).

3. The method of claim 1, wherein the heating of step (b) is from about 5 to about 60 minutes.

4. The method of claim 1, wherein the co-reagent is selected from the group of ketones, enones, and enals consisting of: R-carvone, S-carvone, cyclohex-2-ene-1-one, acetophenone, 3-penten-2-one, butanone, dihydrocarvone, citral, β-ionone, R-pulegone, carvenone, cinnamaldehyde, 3-methylcyclohex-2-enone, pentadione, acetone, piperitone, poperitenone, isopiperitenone, methyl vinyl ketone, butenones, 2-phenylpropenal, and other β-ene-aldehydes.

5. The method of claim 1, wherein the co-reagent is R-carvone, S-carvone, or mixture thereof.

6. The method of claim 1, wherein the co-reagent is dihydrocarvone or carvenone.

7. The method of claim 1 when the amount of co-reagent is from about 1 to about 10 mole equivalents.

8. The method of claim 1 when the amount of co-reagent is from about 3 to about 5 mole equivalents.

9. The method of claim 1, wherein the mixture is heated in a microwave or oil bath.

10. The method of claim 1, wherein, in step (b), the mixture is heated to a temperature of about 180° C. to about 190° C. and is either
    (i) maintained at a temperature of about 180° C. to about 190° C. for about 5 min to about 60 min, or
    (ii) maintained at a temperature of about 190° C. for about 5 min to about 20 min, and if the reaction mixture is not homogenous after the, the mixture is again heated to about 190° C. for about 5 to about 25 min longer.

11. The method of claim 1, further comprising:
    (f) removing unreacted co-reagent or isomerized co-reagent byproduct from the reaction mixture from step (e); and
    (g) recovering the amine salt.

12. The method of claim 11, wherein removing unreacted co-reagent comprises washing the reaction mixture with ether and water and distilling off the water, ether, and co-reagent, to recover the amine salt.

13. The method of claim 1, wherein the acid is any of HCl, $H_2SO_4$, $H_3PO_4$, and HBr.

14. The method of claim 1, wherein the co-reagent is a ketone, enone or enal capable of isomerization at temperatures of about 120° C., or more, to yield a byproduct selected from the group consisting of: enals, enones, phenolic terpenes, phenolic terpenoids, xylenols, and ethylmethylphenols, and
   wherein the acid reaction mixture during step (e) is heated to about 120° C., or more, to hydrolyze the imine to form an amine salt and to isomerize any unreacted co-reagent, the method further comprising:
   (f) extracting the byproduct; and
   (g) recovering the amine salt.

15. The method of claim 14, wherein the co-reagent byproduct is selected from the group consisting of: carvacrol, carvenone, thymol, xylenols, ethylmethylphenols, 2-pentenal, hex-3-en-2-one, piperitone, and 3-ethyl-6-methylcyclohex-2-en-1-one, 3-ethylcyclopent-2-ene-1-one.

16. The method of claim 14, wherein the co-reagent is S-carvone, R-carvone, or dihydrocarvone and wherein the acid reaction mixture during step (e) is heated to about 180° C., or more, to hydrolyze the imine to form an amine and to isomerize any unreacted co-reagent.

17. The method of claim 16, wherein the co-reagent is S- or R-carvone, or a mixture thereof, and wherein the S- or R-carvone is isomerized to produce carvacrol, and further comprising recovering the carvacrol.

18. The method of claim 1, wherein an organic layer containing unreacted co-reagent and an aqueous acid layer form in step (d) and further comprising removing the organic layer before step (e).

19. The method of claim 18, wherein the aqueous acid layer from step (d) is heated during step (e) to about 50 to 80° C., or more, to hydrolyze the imine in equilibrium to form an amine salt, and further comprising:
    (f) removing remaining co-reagent via extraction from the reaction mixture from step (e), and recovering the amine salt.

20. The method of claim 11, further comprising:
    (h) combining the amine salt with a base to yield a corresponding free amine.

21. A method for decarboxylation of amino acids with acid-sensitive side chains, the method comprising:
    (a) combining, in an open reaction vessel, a mixture of an amino acid and a co-reagent, the co-reagent comprising a ketone, enone, enal, aldehyde, or combination thereof, wherein the mixture does not contain a solvent;
    (b) heating the mixture at about 150° C., or more, until the reaction mixture becomes homogenous, wherein the amino acid is converted to its imine;
    (c) cooling the reaction mixture from step (b) in the reaction vessel to a temperature below about 30° C.;
    (d) adding an acid to the cooled reaction mixture from step (c) in the vessel, after which the reaction mixture forms two layers: an organic layer comprising unreacted co-reagent and an aqueous acidic layer comprising the imine;
    (e) removing the organic layer and heating the aqueous acidic layer mixture from step (d) to about 50° C., or more, to hydrolyze the imine to form an amine salt; and
    (f) extracting any remaining co-reagent and recovering the amine salt.

* * * * *